United States Patent
Astarita

(10) Patent No.: US 6,228,059 B1
(45) Date of Patent: May 8, 2001

(54) ENDOSCOPIC INSTRUMENT LOCKS

(76) Inventor: Denis C. Astarita, 801 N. Tustin Ave., Suite 305, Santa Ana, CA (US) 92705

( * ) Notice: Subject to any disclaimer, the term of this patent is extended or adjusted under 35 U.S.C. 154(b) by 0 days.

(21) Appl. No.: 09/334,710

(22) Filed: Jun. 16, 1999

(51) Int. Cl.[7] .................................................. A61M 5/178
(52) U.S. Cl. .............................. 604/164.07; 604/165.01
(58) Field of Search .................................... 604/164, 165, 604/264, 93; 606/167, 170, 172, 185

(56) References Cited

U.S. PATENT DOCUMENTS

| | | | |
|---|---|---|---|
| 4,654,030 | * 3/1987 | Moll et al. | 604/165 |
| 5,066,288 | 11/1991 | Deniega et al. | |
| 5,256,149 | 10/1993 | Banik et al. | |
| 5,399,167 | * 3/1995 | Deniega | 604/165 |
| 5,569,291 | * 10/1996 | Privitera et al. | 606/185 |
| 5,662,613 | 9/1997 | Astarita. | |

* cited by examiner

Primary Examiner—Sharon Kennedy
Assistant Examiner—Catherine Serke
(74) Attorney, Agent, or Firm—James G. O'Neill

(57) ABSTRACT

A locking device for use in a trocar inserted into a body cavity. The locking device include various operating components that may be easily manipulated and recognized by a surgeon during complicated surgery, and a locking portion secured in the trocar. The locking portion may include internal threads formed only on a head, a cam operated element, resilient fingers, a collet-type locking device, or a frictional detent or opening, quickly moved into a locking position against any type of instrument passing through the trocar into the body cavity. The portion of the locking device contacting the instrument must be sized and dimensioned to provide a firm grip in the locking position, without damaging or marring the instrument against which it is locked.

18 Claims, 2 Drawing Sheets

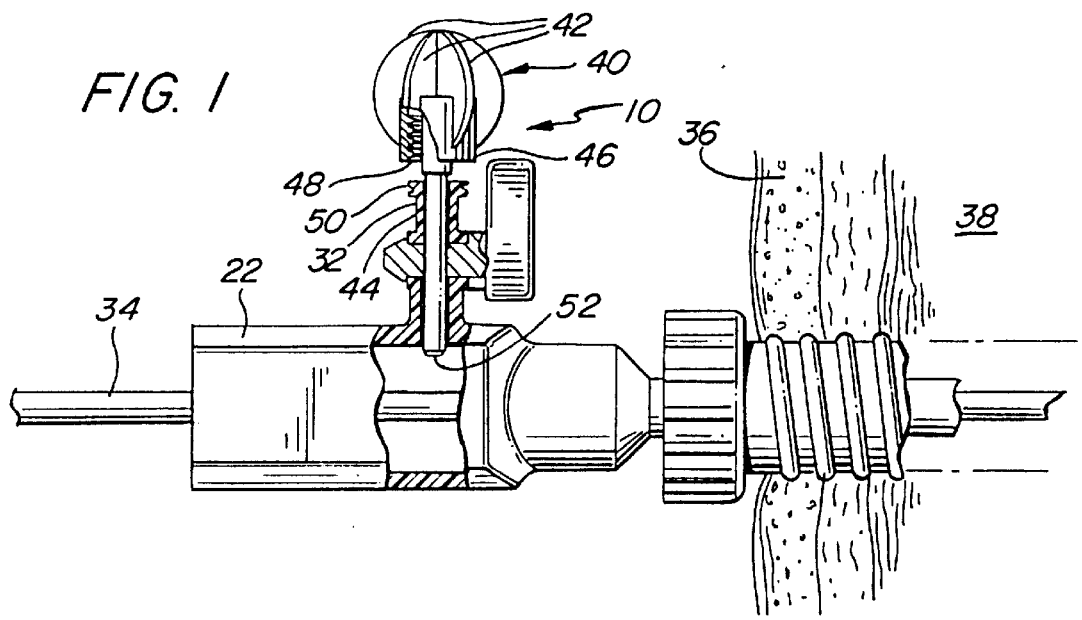
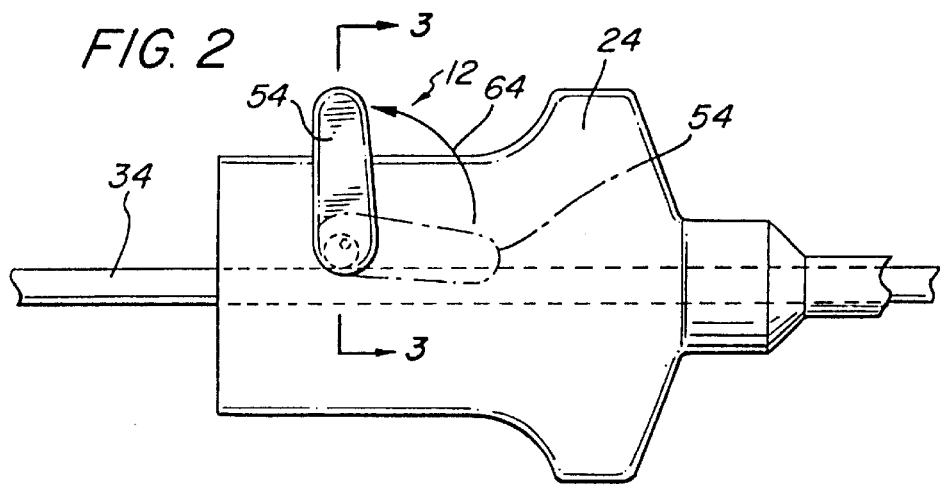
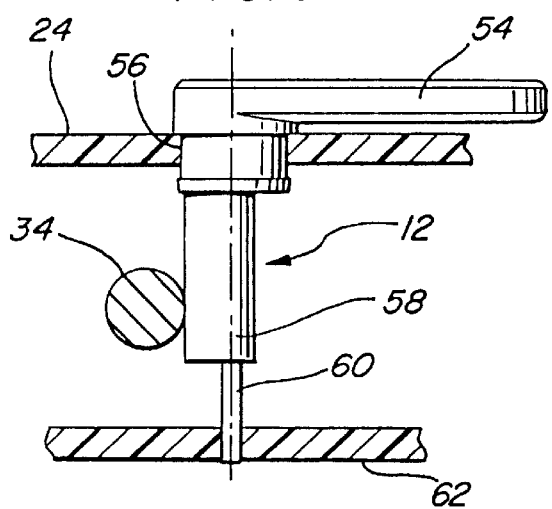

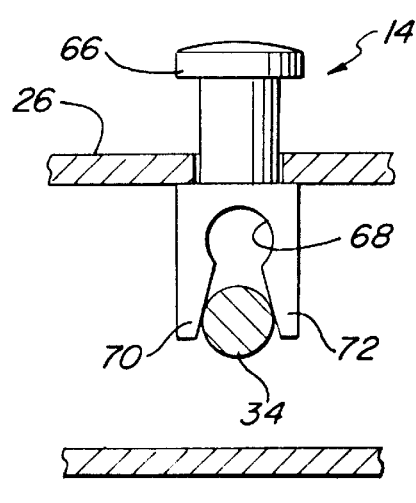
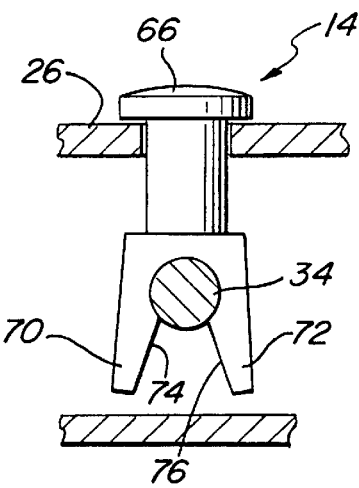
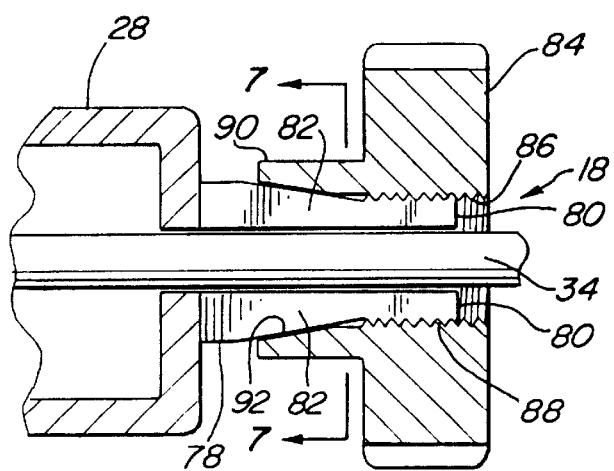
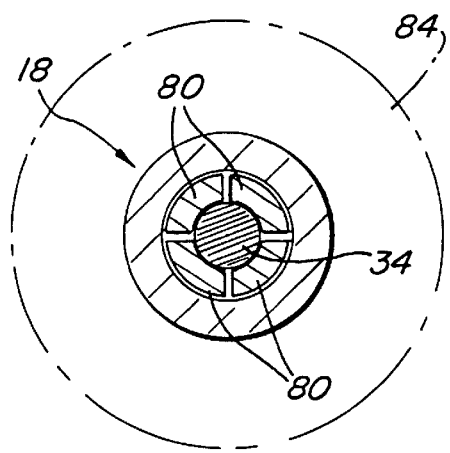
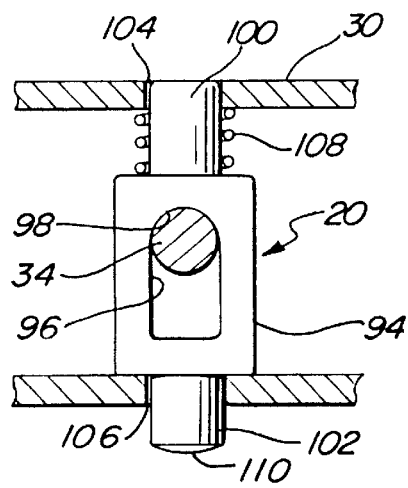
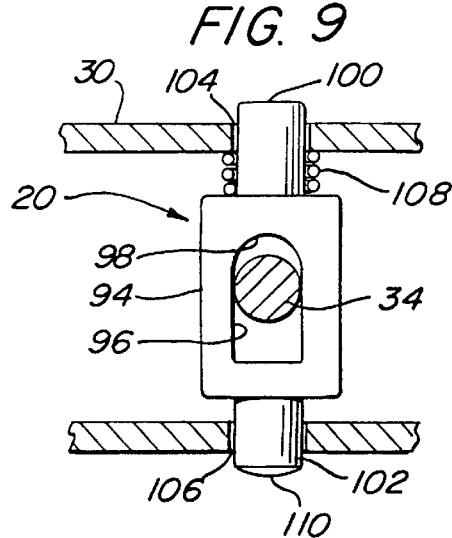

ENDOSCOPIC INSTRUMENT LOCKS

BACKGROUND OF THE INVENTION

1. Field of the Invention

This invention relates generally to trocars for use in endoscopic surgery, and, more particularly, to locking devices for securing in position an instrument inserted through a trocar into a body cavity, so as to prevent movement of the instrument.

2. Description of Related Art

As is well known, surgical devices, such as trocars, are widely used in endoscopic surgery. Trocars are devices that are used to provide access to a surgical site within a selected cavity in a patient's body. A trocar is typically inserted through a small skin incision by pressing the distal end of the trocar against the outer skin of the patient with sufficient force applied to the trocar handle, so that the piercing tip of an obturator effectively penetrates the patient's skin and underlying fat tissue, fascia, muscle and into a selected internal cavity. The trocar obturator is removed, and the trocar cannula is then used as a passageway to and from the patient's body cavity. During many procedures, a number of trocars are required so that a number of passageways are formed into the selected body cavity, to enable a surgeon to concurrently use an endoscope and one or more other devices inserted into the body cavity.

An example of a known trocar is shown in U.S. Pat. No. 5,256,149 to Banik et al. This patent discloses a trocar constructed from a transparent plastic material, and includes a trocar cannula with a cannula handle, a cannula tube and a trocar obturator passing through the handle and tube. The device also includes a gas inlet, having a valve thereon to enable a gas to be used to insufflate and desufflate a body cavity into which the trocar cannula has been inserted and is held, as well as a handle to operate an interior flap valve to release gas pressure in the trocar. After the obturator is used to pierce a person's body and form an opening into an underlying body cavity, the trocar cannula may be threaded into the opening formed into the body cavity with a stability thread to aid in securing the trocar cannula in place. The obturator is removed from the trocar cannula, and an instrument, such as an endoscope, an endoscopic needle grasper, a holding device, a manipulating device, or the like, may be inserted through the trocar cannula into the body cavity.

During many types of surgery, a number of trocars are inserted so that there are a number of passageways into the selected body cavity. One or more of these passageways may be used to move or position an organ if a further portion thereof must be seen or operated on. In addition, the organ may cover or block another organ, which needs to be examined or operated on. This is usually accomplished by the insertion of a grasping or manipulating device or instrument, into a passageway in one of the trocars. However, the grasping or manipulating instrument is usually loosely aligned in the trocar passageway, and must be held in position or somehow secured, so that any organ, or the like, that is pressing against or supporting, does not move or shift. Since the surgeon and/or assistant must concentrate on specific steps and requirements during a surgical procedure, and often need both of their respective hands, a holding means or another person must help to hold or support the grasping or manipulating device. Often, however, it is left to the surgeon or assistant to try to hold the instrument steady by the use of a surgical clamp between the instrument and a surgical drape on the patient, or somehow jury-rig a means to hold or support the instrument. For numerous reasons, surgeons and their assistants have difficulty in fully or properly holding or supporting such grasping or manipulating device, and problems have occurred. Therefore, a need exists for a simple and effective means for holding a grasping or manipulating device or instrument in place in a trocar during surgical procedures, such as endoscopic surgery.

In my U.S. Pat. No. 5,662,613 ("'613"), entitled "Endoscopic Instrument Lock", there is described and shown a locking device for use in holding an instrument in place in a trocar. This locking device is preferably metallic, and includes an enlarged head that may be easily grasped and recognized by a surgeon during surgery. The device has an elongated shaft portion with self-taping threads formed thereon, secured to the enlarged head. The outer end of the elongated shaft is blunt and soft to prevent damage or marring of an instrument against which it is pressed. The elongated shaft is inserted into the existing gas opening in the wall of the trocar and the enlarged head turned so that the self-tapering threads are threaded into the existing gas opening to lock the device into position with the blunt, soft end against an instrument. The enlarged head is preferably knurled, roughened or serrated to enable the locking device to be easily grasped and turned by the fingertips of a user. The spherical head is also preferably made from or covered with a phosphorescent material so as to be more easily seen in low lighting conditions. Although this locking device has provided significant improvement in the art, there is a possibility that if it is carelessly handled or manipulated, foreign or toxic material might be dislodged or inserted into the gas opening and enter a body cavity of a patient.

Furthermore, the locking device of the '613 patent must be stored before or after use, and is not always immediately available for use, unless placed in the gas opening of the trocar or trocars, before, during or after being inserted into a body cavity.

Therefore, there still exists a need in the art for easy to use and readily available locking devices for instruments inserted into a trocar, and, in particular, locking devices that are not easily laid aside or misplaced.

SUMMARY OF THE INVENTION

Accordingly, it is a general object of the present invention to provide an improved instrument locking means. It is a particular object of the present invention to provide an improved instrument-locking device, which is easy to manufacture and use. It is another particular object of the present invention to provide an improved instrument-locking device, which is readily available for use with a trocar. It is yet another particular object of the present invention to provide an improved instrument-locking device, which is formed with or in a trocar. It is a further object of the present invention to provide an improved instrument-locking device, which is readily available and easily operated in a darkened operating room. It is yet another object of the present invention to provide an improved locking device held in a trocar, which locking device is capable of being manufactured with the trocar. And, it is still another particular object of the present invention to provide an improved locking means for trocars, which are secured to the trocar and cannot be misplaced or lost.

In accordance with one aspect of the present invention, there is provided a locking element for a trocar, to hold an instrument in place. The locking element is quickly and easily operated, and is held in the trocar, where it may be easily grasped and used by a surgeon or assistant during surgery. The locking element is held in position in the trocar so as to lock an instrument inserted into the trocar, without fumbling or searching for the locking device. The locking device cooperates with the instrument in the trocar, without damaging or marring the instrument.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, wherein like reference numerals are used throughout the several views, and, in which:

FIG. 1 is a perspective view of a prior art trocar inserted into a body cavity with a grasping or manipulating instrument inserted through the trocar into a body cavity, and also showing a first embodiment of the locking device of the present invention, held in a gas opening before it is locked into position in the trocar for locking the instrument in position, and preventing movement thereof;

FIG. 2 is a top plan view of a second embodiment of a locking device built into a trocar for locking instrument in the trocar;

FIG. 3 is an enlarged cross-sectional view taken along line 3—3 of FIG. 2;

FIG. 4 is a partial cross-sectional view of a trocar with a grasping or manipulating instrument inserted therein, having a third embodiment of a locking device held in the trocar and in position to be pressed down to lock the instrument in position;

FIG. 5 is a partial cross-sectional view, similar to FIG. 4, with the locking device in the locking position around the instrument;

FIG. 6 is a partial cross-sectional view of a trocar with a grasping or manipulating instrument inserted therein, and passing through a fourth embodiment of the locking device, in the form of a collet-type lock;

FIG. 7 is a cross-sectional view taken along line 7—7 of FIG. 6;

FIG. 8 is a partial cross-sectional view of a trocar with a grasping or manipulating instrument inserted therein and having a fifth embodiment of the locking device in a locking position against the instrument; and FIG. 9 is a partial cross-sectional view, similar to FIG. 8, with the locking device in an open or unlocked position to allow the instrument to move therein.

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to described instrument locking devices or means, identified generally at 10, 12, 14, 18, 20 for use in trocars, such as 22, 24, 26, 28, 30. For example, locking device 10 may be inserted in an existing gas opening 32 in the trocar 22 to hold or lock an instrument, such as 34, with respect to the trocar. For reasons of explanation only, and not by way of limitation, the locking device 10 is described and shown herein for use in a specific trocar, such as described and claimed in U.S. Pat. No. 5,256,149 ("'149") to Banik et al., having a transparent plastic body. The relevant portions of this '149 patent are incorporated herein, in their entirety, by this reference thereto. It is to be understood, that the present invention provides locking devices or means for use in any existing trocar or similar surgical instrument, and which may be inserted or built into any such surgical instrument, requiring a means or locking device to hold an instrument inserted therein in an immovable or locked position during surgery.

Since only one of the gas inlets of a plurality of trocars must be used to insufflate and desufflate the internal body cavity, if a plurality of trocars are inserted into a selected body cavity, one or more of the other gas inlets may be provided with a locking means 10 inserted therein.

As shown in FIG. 1 of the drawings, after a trocar cannulas 22 has been inserted through a skin layer, etc. 36, so as to be connected to an internal cavity 38 and an obturator (not shown) removed in a manner well known to those skilled in the art, the instrument 34 is inserted through a passage in the trocar. After the instrument 34 is inserted and moved or manipulated to a preferred or selected position, the locking means 10 may be turned so as to lock the instrument against further movement, with respect to the trocar. The further locking means 12, 14, 18 and 20, described below, are also operated to lock the instrument 34. The locking of instrument 34 frees up the hands of a surgeon, or the surgeon's assistant, to perform the rest of the surgical procedure through one or more other trocars, not shown, in an expeditious and safe manner.

The locking device or element 10 has an actuating or operating element 40, such as an enlarged head, with a plurality of grasping elements or vanes 42. The head 40 is secured to an elongated shaft 44. A lower end 46 has an internally formed ramp, threads, or the like, 48 formed therein, so as to form a locking element that is termed a "Luer-type Lock". The "Luer-type Lock" 48 allows the operating element 40 to be easily operated by turning, so that the "Luer-type Lock" moves over an outer end or lip 50 of the gas opening 32, in a manner well known to those skilled in the art. By using a Luer-type lock, the danger of toxic material entering the trocar 22 is substantially eliminated.

As disclosed in the '149 patent, the housing of the trocar cannulas, including the valve and gas opening 14, are manufactured from plastic. However, the locking device 10, including head 40, the shaft 44 and the lock 48 may be formed from any desired material, such as stainless steel, or other plastic or metal material. As is often the case, the material used may be coated or uncoated, as long as it may be easily sterilized and is approved for medical use. The selected material must also allow the locking element 10 to be quickly and easily engaged, when the Luer-type lock 48 is moved over the end 50, by turning head 40. The locking device 10 will, therefore, be quickly inserted and then turned, so that the locking element or shaft 44 moves downwardly or inwardly, into the gas inlet 32, until the lower or outer end 52 is brought into contact with the instrument 34. The outer end 52 is preferably blunt and softened, so that when it moves into contact with the instrument 34, it will not damage, mar or mark the same, and so that it will have a larger contact surface which will frictionally engage instrument 34, to prevent it from moving, with respect to the trocar 22.

Turning now to FIGS. 2 and 3, there shown is a second embodiment of the locking device 12, which is preferably added to or built into the trocar cannulas 24. This locking device 12 includes an actuating or operating element 54, such as a handle, held on the outside of the trocar 24. The handle 24 is rotatably and sealingly held in an opening 56 in a first wall of trocar cannulas 24, and is connected to, or formed integrally with a locking element 58, such as an offset cam element, and a lower holding shaft 60, which is also rotatably mounted within an opposite or second wall 62 of the trocar cannulas 24. The offset cam element 58 is moved by turning the handle 54, between an unlocked position, where it is spaced from the instrument 34, as shown in broken line in FIG. 2, to a locked position, as shown in solid line in FIGS. 2 and 3, where the cam element 58 is pressed against the instrument 34 to lock the instrument and prevent it from moving. Arrow 64 in FIG. 2 indicates the direction of movement of the handle 54 from the open position (broken line) to the locked position (solid line).

Referring now to FIGS. 4 and 5, there shown is a third embodiment of the locking device 14, which is preferably built into the trocar cannulas 26. The locking device 14 includes an actuating or operating element 66, such as a handle or push button, and a locking element having an open, partially curved or cylindrical central portion 68 and a pair of resilient arms or fingers 70, 72. As shown, the operating element 66 is pressed downwardly or inwardly, from the position shown in FIG. 4, into the trocar cannulas 26, to the position shown in FIG. 5, to lock the instrument 34 against movement. As the operating element 66 moves into the trocar cannulas 26, angled inner sides 74, 76 of the resilient arms or fingers 70, 72 contact the instrument 34. The arms or fingers are cammed or pushed outwardly by the instrument 34, until the instrument enters open partially cylindrical central portion 68, where the instrument is clamped, held or locked immovably in position, until the element 66 is pulled out or retracted. It is to be understood, that the open, partially curved or cylindrical central portion 68 and the resilient arms 70, 72, as well as the angled sides 74, 76, are sized and dimensioned so as to cooperate with instruments, such as 34, which are inserted in trocars, to securely clamp, hold or lock the instrument in place when pushed onto or otherwise forced onto the instrument. Furthermore, the parts of the lower locking element must be sized and dimensioned to enable the resilient arms 70, 72 to be sufficiently withdrawn, to release the instrument 34 when element 66 is moved or withdrawn to its open position (FIG. 4).

FIGS. 6 and 7 show a still further or fourth embodiment of the locking device 18, built into the trocar cannulas 28. This locking device 18 is a collet-like device, which is formed in or around an entrance or exit opening of the trocar cannulas 28. The locking device 18 includes a locking element or portion 78 having a plurality of resilient arms or fingers 80 (four are shown), with angled or tapered outside edges 82, as shown in FIG. 6. An actuating or operating element 84, such as a handle or ring, having internal threads 86 is held on external threads 88 formed on an exterior surface of each of the fingers 80, adjacent outer ends of the fingers. The turning ring 84 also includes an annular extending portion 90 formed therein, after the internal threaded portion 86. The annular extending portion 90 includes an internal tapered wall 92, which cooperates with the angled or tapered outside edges 82 of the fingers 80. The collet-type locking device 18 is operable between an open position, as shown in FIG. 6, to a locking position, as illustrated in FIG. 7, by turning the handle or ring 84. That is, when turned in one direction, the threads 86, 88 will cooperate to move the annular extending portion 90 inwardly or a first direction, to force the tapered wall 92 against the angled sides 82, to move the fingers 80 inwardly, to clamp, hold or lock the instrument 34 in position. However, when turned in the other direction, the annular extending portion 90 will move outwardly, or in a second direction, to move the tapered wall 92 away from the angled sides 82 of the resilient fingers 80, to thereby allow the resilient fingers 80 to move away or spring back from their locked position against the instrument.

Turning now to FIGS. 8 and 9, there shown is a fifth embodiment of the locking device 20, which is preferably built into the trocar cannulas 30. This locking device 20 includes a locking element 94, such as a central element or portion having an aperture or opening 96 with a curved or semi-circular top portion 98 formed in the opening. The curved or semi-circular top portion 98 is sized and dimensioned to frictionally cooperate with and hold the instrument 34 in position, when biased or pressed against the same, as shown in FIG. 8. The central element 94 is preferably sized and dimensioned and made from a material which will engage the instrument 34 with sufficient friction when the curved or semi-circular top portion 98 is biased or pressed against the instrument, to lock or prevent movement thereof. The locking element 94 is connected or secured to two aligned elements or shafts 100, 102, at opposite ends or sides thereof. These shafts are inserted and sealingly held in openings 104, 106, formed in opposite walls of the trocar cannulas 30. A biasing means 108, such as a spring 108 is mounted over the first shaft 100, and normally biases the locking element 94 into the locked position, with the curved or semi-circular end 98 pressed against the instrument 34, which is inserted in the opening 96. An actuating or operating element is provided to open or unlock the locking device 20, for insertion of instrument 34 into opening 96 or movement of the instrument within the trocar cannulas 30. This actuating or operating element is comprised of an outer end 110 of shaft 102, which is pressed or pushed inwardly toward the trocar, to compress the spring 108 and move semi-circular end 98 away from instrument 34, as shown in FIG. 9.

As described above, the locking devices 10, 12, 14, 18, 20 of the present invention are inserted into an existing gas opening in a trocar cannulas, or are added to or built into a trocar cannulas. The locking devices 10, 12, 14, 18 and 20 are then readily available and accessible to a surgeon or an assistant during a surgical procedure, for operating or tightening the same. The surgeon or the surgeon's assistance's hands are thereby left free for more important tasks. Because of their availability, size and easy operation, the locking devices of the present invention, may be conveniently operated in a trocar in critical situations without requiring any special tools, adjustments, or changes to existing equipment. Furthermore, the locking devices of the present invention are easily and quickly operated to lock or unlock an instrument, as needed.

Thus, it can be seen, that the locking devices of the present invention provide locks that are compatible with existing trocar cannulas and/or new trocar cannulas, and which are easily installed at a point-of-use, or by a manufacturer of trocars, at the factory when assembling the trocar cannulas.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A trocar assembly comprising:

an elongate trocar obturator having a proximal end and a distal end with a piercing tip thereon;

an elongate trocar cannula having an interior passage therethrough for receiving the trocar obturator; the elongate trocar cannula having an elongate cannula tube and a trocar handle for mounting the elongate cannula tube;

at least a portion of a locking device being held in the trocar handle for holding a separate surgical instrument in the interior passage while the elongate trocar obturator is in a position removed from the interior passage;

the locking device including an operating portion held on an exterior portion of the trocar handle; a holding portion secured to the operating portion and held internally in the trocar handles and having a securing portion adapted to cooperate with the separate surgical instrument to lock the separate surgical instrument in the interior passage; and wherein, while the obturator is removed from the interior passage, the operating portion is movable between an open position allowing the separate surgical instrument to be inserted and moved within the interior passage and a locked position where the holding portion firmly abuts the separate surgical instrument to prevent movement of the separate surgical instrument within and relative to the interior passage.

2. A trocar assembly comprising:

an elongate trocar obturator having a proximal end and a distal end with a piercing tip thereon;

an elongate trocar cannula having an interior passage therethrough for receiving the trocar obturator; the elongate trocar cannula having an elongate cannula tube, a trocar handle for mounting the elongate cannula tube and at least a portion of a built-in locking device in the trocar handle;

the built-in locking device adapted to hold a separate surgical instrument in the interior passage while the elongate trocar obturator is in a position removed from the interior passage;

the built-in locking device including an actuating element secured to a holding element, which holding element is held internally in the trocar handle, and has a securing portion adapted to cooperate with the separate surgical instrument to lock the separate surgical instrument in the interior passage; and wherein, while the elongate trocar obturator is removed from the interior passage, the actuating element is movable between an open position allowing the separate surgical instrument to be inserted and moved within the interior passage and a locked position where the holding portion firmly abuts the separate surgical instrument to prevent movement of the separate surgical instrument within and relative to the interior passage.

3. A trocar assembly comprising:

an elongate trocar obturator having a proximal end and a distal end with a piercing tip thereon;

an elongate trocar cannula having an open interior passage therethrough for receiving the trocar obturator; the elongate trocar cannula having an elongate cannula tube, a trocar handle for mounting the elongate cannula tube and at least a portion of a built-in locking device in the trocar handle;

the built-in locking device adapted to hold a separate surgical instrument in the open interior passage while the elongate trocar obturator is in a position removed from the open interior passage;

the built-in locking device including an operating element mounted on an exterior surface of the trocar handle;

a shaft rotatable secured in the trocar handle, with a first end of the shaft held in a first internal wall of the trocar handle and a second end of the shaft extending through a second internal wall of the trocar handle and operatively connected to the operating element;

an offset cam formed on the shaft between the first internal wall and the second internal wall;

the offset cam being movable between locked and unlocked positions by manipulation of the operating element; and wherein, while the elongate trocar obturator is removed frown the interior passage, the offset cam frictionally locking the separate surgical instrument in the open interior passage, when the offset cam is in the locked position.

4. The trocar assembly of claim 1 wherein the operating portion is an enlarged head having a plurality of vanes for easy gripping thereof, which enlarged head includes means formed therein for cooperating with a top of a gas passage formed in the trocar cannula, and the holding portion is an elongated smooth shaft extending through the gas passage having a soft blunt end, which contacts the instrument in the trocar cannula.

5. The locking device of claim 1 wherein the operating portion is a push button, and the holding portion is a pair of resilient arms with an opening formed therebetween.

6. The lock device of claim 5 wherein the resilient arms include angled inside edges which cooperate with the separate surgical instrument so as to cam open the resilient arms and allow the separate surgical instrument to enter the opening, and wherein the separate surgical instrument is clamped by the resilient arms when in the opening.

7. The locking device of claim 1 wherein the operating portion is an elongated arm, and the holding portion is an offset cam rotatably held between internal side walls of the trocar cannula.

8. The locking device of claim 1 wherein the operating portion is a handle having internal threads, and the holding portion is a plurality of resilient fingers having external screw threads on outer ends thereof.

9. The locking device of claim 8 wherein the handle is ring-shaped, and includes an annular extending portion cooperate with angled sides formed on the plurality of resilient fingers so as to move the resilient fingers between opened and closed positions, by turning the ring-shaped handle.

10. The locking means of claim 1 wherein the operating portion is a push button, and the holding portion is a curved portion formed in an opening.

11. The locking means of claim 10, further including a shaft having a biasing means mounted thereon for biasing the holding portion into the locking position.

12. The locking device of claim 11, further including a central portion held between the push button and the shaft; the central portion having the opening formed therein and a spring is held between the upper surface of the central portion and a guide shaft so as to bias the central portion into the locking position.

13. The trocar assembly of claim 2 wherein the actuator element is a push button movable from an opened position in a wall of the trocar cannula to the locked position in the trocar cannula.

14. The built-in locking device of claim 13 wherein the holding element includes a pair of resilient arms having angled interior side edges and a partially cylindrical holding portion therebetween; and wherein the separate surgical instrument is insertable between the resilient arms so that the angled side edges press against the separate surgical instrument so as to cam the resilient arms away from each other, upon pushing of the push button into the trocar cannula, to lock the separate surgical instrument in the partially cylindrical holding portion.

15. The built-in locking device of claim 13 wherein the holding element comprises a central element having a guide shaft secured thereto and held in a wall of the trocar cannula opposite a wall in which the actuating element is held, and wherein the central element includes a central open portion having a curved top which is biased into engagement with the separate surgical instrument to lock the separate surgical instrument in position.

16. The built-in locking device of claim 15, further including a spring element mounted around the guide shaft for normally biasing the central element into the locked position, and whereby the actuating element is a push button connected to the central element, and the push button extends outwardly from a wall of the trocar cannula when in the closed position.

17. The built-in locking device of claim 2 wherein the actuating element is a ring element, having internal threads and an annular extending portion with an internal tapered wall, and the holding element includes a plurality of resilient fingers with external threads cooperating with the internal threads, and tapered side edges cooperating with the internal tapered wall; whereby, upon turning of the ring element, the locking device will be locked or unlocked.

18. The built-in locking device of claim 2 wherein the actuating element is an elongated arm on the exterior of the trocar cannula, and the holding element is comprised of an offset cam element mounted on a shaft rotatably held between internal side walls of the trocar cannula by portions of the shaft extending through the internal side walls.

* * * * *